United States Patent
Kolter et al.

(10) Patent No.: US 11,123,282 B2
(45) Date of Patent: Sep. 21, 2021

(54) FORMULATIONS WITH A CONTROLLED RELEASE OF PERFUMES FOR DERMAL APPLICATION

(71) Applicant: BASF SE, Ludwigshafen am Rhein (DE)

(72) Inventors: Karl Kolter, Limburgerhof (DE); Ralf Pelzer, Fuerstenberg (DE); Marion Bendel, Ludwigshafen (DE); Matthias Karl, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/768,645

(22) PCT Filed: Oct. 13, 2016

(86) PCT No.: PCT/EP2016/074595
§ 371 (c)(1),
(2) Date: Apr. 16, 2018

(87) PCT Pub. No.: WO2017/067843
PCT Pub. Date: Apr. 27, 2017

(65) Prior Publication Data
US 2019/0060209 A1  Feb. 28, 2019

(30) Foreign Application Priority Data
Oct. 23, 2015  (EP) .................................... 15191157

(51) Int. Cl.
| | |
|---|---|
| *A61K 8/04* | (2006.01) |
| *A61K 8/81* | (2006.01) |
| *A61Q 13/00* | (2006.01) |
| *A61K 9/00* | (2006.01) |
| *A61K 47/08* | (2006.01) |
| *A61K 9/08* | (2006.01) |
| *A61K 47/10* | (2017.01) |
| *A61K 9/12* | (2006.01) |
| *A61K 8/25* | (2006.01) |
| *A61K 8/34* | (2006.01) |

(52) U.S. Cl.
CPC ............ *A61K 8/8135* (2013.01); *A61K 8/046* (2013.01); *A61K 8/25* (2013.01); *A61K 8/34* (2013.01); *A61K 8/342* (2013.01); *A61K 8/81* (2013.01); *A61K 8/8176* (2013.01); *A61K 9/0014* (2013.01); *A61K 9/08* (2013.01); *A61K 9/12* (2013.01); *A61K 47/08* (2013.01); *A61K 47/10* (2013.01); *A61Q 13/00* (2013.01)

(58) Field of Classification Search
CPC ..................................................... A61K 8/342
See application file for complete search history.

(56) References Cited

U.S. PATENT DOCUMENTS

| | | | |
|---|---|---|---|
| 4,803,195 A | 2/1989 | Holzner | |
| 5,508,259 A | 4/1996 | Holzner et al. | |
| 6,172,037 B1 | 1/2001 | Perring et al. | |
| 2004/0001891 A1* | 1/2004 | Smith | A61K 8/0229 424/469 |
| 2006/0115529 A1* | 6/2006 | Jeong | A61K 47/585 424/464 |
| 2006/0193812 A1 | 8/2006 | Holzner et al. | |
| 2006/0287352 A1* | 12/2006 | Holm | A61K 9/0053 514/291 |
| 2014/0017287 A1* | 1/2014 | Lei | B01J 13/14 424/401 |
| 2017/0216166 A1* | 8/2017 | Sasaki | A61Q 5/02 |

FOREIGN PATENT DOCUMENTS

| | | | |
|---|---|---|---|
| CA | 2008556 A1 | 8/1990 | |
| EP | 0 384 034 A2 | 8/1990 | |
| EP | 0384034 A2 * | 8/1990 | ............... A61K 8/11 |
| WO | WO-2005/055964 A1 | 6/2005 | |

OTHER PUBLICATIONS

English Machine Translation of EP 0 384 034 A2. Obtained Jun. 27, 2019 from https://worldwide.espacenet.com/publicationDetails/claims?CC=EP&NR=0384034A2&KC=A2&FT=D&ND=3&date=19900829&DB=EPODOC&locale=en_EP# (Year: 1990).*

International Search Report for PCT Patent Application No. PCT/EP2016/074595, dated Nov. 25, 2016.

* cited by examiner

*Primary Examiner* — Arrie L Reuther
(74) *Attorney, Agent, or Firm* — Marshall, Gerstein & Borun LLP

(57) ABSTRACT

An odorant and flavoring formulation for topical application comprising, as matrix former, a mixture of at least one water-insoluble polymer from the group of homo- or copolymers of C1-C4-carboxylic acid vinyl esters and at least one water-soluble polymer from the group of homo- or copolymers of N-vinyllactams.

10 Claims, No Drawings

FORMULATIONS WITH A CONTROLLED RELEASE OF PERFUMES FOR DERMAL APPLICATION

CROSS-REFERENCE TO RELATED APPLICATIONS

This is the U.S. national phase of International Application No. PCT/EP2016/074595, filed Oct. 13, 2016, which claims the benefit of European Patent Application No. 15191157.5, filed on Oct. 23, 2015.

The present invention relates to formulations with controlled release of odorants for dermal application, wherein the odorants are embedded in a matrix based on homo- or copolymers of vinyl esters.

Odorants are typically applied to the skin as an alcoholic solution. On account of their relatively low boiling point, they volatilize and in this way produce a certain odor when inhaled. The volatilization is further enhanced by the skin temperature of ca. 32° C. and the relatively large surface area of the skin and the hair thereon. By virtue of these factors the perfumes even after a short time are frequently no longer intensively perceived. In addition to this, the odorants are generally used as a mixture of numerous components, in the form of a perfume for example, all of which have a different boiling point and therefore a different volatility. As a result, the odor of the perfume alters in the course of use, since the more volatile components evaporate first.

According to the prior art, the delayed release of odorants was primarily achieved by means of microencapsulation. For this purpose, intermediate emulsions are generally prepared which are subsequently partly dried before they are processed to the final formulation. Such formulations are described, for example, in documents U.S. Pat. No. 4,803,195, US 2006/0193812, WO 2005/055964, US 2004/0001891, EP 0384034 or U.S. Pat. No. 5,508,259.

However, these formulations have the disadvantage that they are biphasic systems which are therefore automatically physically unstable. Furthermore, the preparation is correspondingly complex, since the odorant has to be dispersed and enveloped. A heterogeneous system is therefore also present on the skin. The emulsifiers used are also frequently skin irritants.

Therefore, there is a necessity to develop formulations which do not have these disadvantages. It is of crucial importance that the preparation can be readily applied to the skin and forms a depot there in a relatively short time, that it persists a long time, is invisible or barely visible, is not readily washed off by water and has a certain resistance to sweat but can be easily removed again by soap solution.

The depot formulations applied must also have a certain water vapor permeability so that no moisture depot forms underneath them, which can lead to their detachment. A significant adhesion capacity on the skin is therefore also required.

Water-soluble polymers alone are unsuitable for the purpose specified since they are dissolved by the sweat production of the skin and become sticky owing to their hygroscopicity. They therefore produce an unpleasant skin feel and may also adhere to clothing.

This problem was solved in accordance with the invention by incorporating polymers with specific properties and developing specific dosage forms and application forms.

Accordingly, formulations for topical application have been found for the controlled release of odorants and flavorings, comprising at least one synthetic odorant and flavoring and, as matrix former, a mixture of at least one water-insoluble polymer from the group of homo- or copolymers of C1-C4-carboxylic acid vinyl esters and at least one water-soluble polymer from the group of homo- or copolymers of N-vinyllactams.

Water-insoluble homopolymers of vinyl esters such as polyvinyl acetate, polyvinyl propionate, polyvinyl butyrate, or also copolymers of vinyl esters with acrylic esters or vinyllactams, can have molecular weights of 10 000 to 1 000 000 daltons. In the copolymers with vinyllactams, the proportion by mass of vinyl ester must be greater than 50% so that the polymer is water-insoluble. The proportion by mass of vinyl esters is preferably greater than 80%, particularly preferably greater than 90%.

In accordance with the invention, water-insoluble signifies that not more than 10 g dissolve in 1 l of water under standard conditions (20° C., 0.1013 MPa).

According to a preferred embodiment, the odorant formulations comprise a polyvinyl acetate having an average molecular weight $M_w$ of 200 000 to 700 000 daltons as water-insoluble polymer.

The water-soluble polymers used for the formulations comprise homopolymers of vinyllactams and copolymers of vinyl esters with vinyllactams having a molecular weight between 5000 and 1 000 000 daltons. In the case of the copolymers with vinyllactams, the proportion of vinyllactam must be greater than 50% in order to ensure sufficient water solubility. Suitable copolymers are, for example, those that are obtained from 60 wt % N-vinylpyrrolidone and 40 wt % vinyl acetate. Preferred water-soluble polymers are homopolymers of N-vinylpyrrolidone with K values according to Fikentscher (measured in water) of 12 to 120, particularly 15 to 50, especially preferably K30.

According to a preferred embodiment, mixtures of polyvinyl acetate and polyvinylpyrrolidone are used for the polymer matrix that have a K value according to Fikentscher of 30, especially mixtures comprising a polyvinyl acetate having an average molecular weight Mw of 200 000 to 700 000 daltons as water-insoluble polymer and a homopolymer of N-vinylpyrrolidone having a K value of 30 as water-soluble polymer.

According to a preferred embodiment, the mixtures of polyvinyl acetate and polyvinylpyrrolidone additionally comprise 0.1 to 2 wt % sodium dodecylsulfate, based on the solids content of the formulation. According to a further particularly preferred embodiment, the mixtures of polyvinyl acetate and polyvinylpyrrolidone additionally comprise 0.1 to 2 wt % sodium dodecylsulfate, based on the solids content of the formulation, and additionally 0.05 to 2 wt % silicon dioxide, based on the solids content of the formulation.

The matrix mixtures used according to the invention of water-insoluble polymers such as polyvinyl acetate and water-soluble polymers such as polyvinylpyrrolidone can be obtained in various ways. The mixtures may either be used as pre-formulated powder or be prepared directly in a usable solution.

For instance, the water-soluble polymers and optionally further additives may be added to an aqueous dispersion of the water-insoluble polymer. Furthermore, an aqueous dispersion of the water-insoluble polymers may be prepared from the outset using the water-soluble polymers as protective colloid. Surface-active compounds such as sodium dodecylsulfate may also be added to the aqueous dispersion of the water-insoluble polymers.

To an aqueous dispersion of this kind can then be added an additional amount of a water-soluble polymer.

The aqueous dispersions used in accordance with the invention, comprising the water-insoluble and water-soluble polymers, may also be converted to powder form by customary spray processes.

According to another embodiment, it is possible to obtain the mixtures of water-insoluble and water-soluble polymers by co-dissolving the respective pulverulent polymers in a suitable organic solvent or aqueous/organic solvent mixture. Subsequently, the solvent can be removed by suitable processes such as spray processes or evaporation processes in order to obtain again a pulverulent matrix mixture.

Particularly suitable mixtures are commercially available, for example as Kollicoat® SR30D or Kollidon® SR.

Furthermore, it is also possible to use various other auxiliaries in order to further modify and improve the properties of the administration form. For instance, colorants may be added, particularly preferred colorants being those which produce the color of the skin.

Additional auxiliaries which may be used are: stabilizers, preservatives, plasticizers, emulsifiers, solubilizers, surface-active substances, spreading agents, substances for adjusting viscosity, substances for improving atomization.

It is possible to incorporate odorants of various type and number of individual synthetic odorants, for example geraniol, linalool, linalyl acetate, pyranol, geranyl acetate, anisaldehyde, citral, citronellal, lysmeral, citronellol, rose oxide, tetrahydrolinalool, hydroxycitronellal, beta-ionone or menthol, up to complex perfume compositions or insect repellents. Preference is given to geraniol, linalool, linalyl acetate, pyranol, geranyl acetate, anisaldehyde, citral, citronellal, lysmeral, citronellol, rose oxide, tetrahydrolinalool, hydroxycitronellal, beta-ionone or menthol. Particular preference is given to geraniol, linalool or menthol.

The formulations according to the invention are generally in the form of solutions in compatible organic solvents. Such solvents are, for example, ethanol, propanol, iso-propanol, esters such as ethyl acetate, dimethyl ether, pentane, propane, butane, iso-butane, halogenated propellant gases or mixtures of these substances. Here, the water content of the preparations is less than 30%, preferably less than 20% and particularly preferably less than 10%. Since the formulations are monophasic systems, the formulations according to the invention are physically extremely stable.

A further embodiment of the invention relates to odorant formulations. Formulations of this kind comprise (i) 0.5 to 10 wt % matrix formers, (ii) 60 to 99.4 wt % solvent, and (iii) 0.1 to 20 wt % of one or more odorants, where the amounts are based the total weight (100 wt %) of the formulation. Preferred formulations comprise (i) 1.0 to 5 wt % matrix formers, (ii) 70 to 98.5 wt % solvent, and (iii) 0.5 to 10 wt % of one or more odorants.

The preparations according to the invention may be applied or else sprayed onto the skin by means of various applicators. By means of the proportion of organic solvent, which rapidly evaporates, a thin film forms in a short time, which functions as a depot. The application-ready formulations may therefore be supplied as a pump spray, aerosol spray, dropping solution or solution. The film that forms on the skin or on the hair is clear, transparent, not sticky, invisible or barely visible and extremely flexible, does not produce a feeling of tightness in the skin on movement and releases the odorant in a retarded manner.

In the case of particularly high loading with odorants or the use of insoluble auxiliaries, the liquid preparation may also consist of a biphasic system, consequently an emulsion or dispersion, which is then stabilized by emulsifiers and dispersants. The emulsion droplets or solid particles are embedded in the film on the skin ultra finely distributed in the polymer.

The technology described may also be used to apply insect repellents on human or animal skin. In this manner prolonged protection is achieved.

The preparations according to the invention also enable treatment of textiles, in which case similar effects also occur here, such as, for example, no visibility, retarded release of the odorants and easy washability in washing machines.

Surprisingly, polyvinyl esters are highly compatible with different odorants, specifically both in alcoholic solution and in the form of a film.

The properties of the films can be adjusted by combination of the water-insoluble polymers with water-soluble polymers, in which case the polymer types must be highly compatible, since otherwise opaque films are formed rather than transparent films.

Surprisingly, the odorants have high affinity for the polymers and as a result these are released in a retarded manner over a prolonged period of time.

EXAMPLES

Kollidon® SR:

80% polyvinyl acetate (MW 450 000 D), 19% Povidone K30, 0.8% sodium laurylsulfate and 0.2% silica Kollicoat® SR30D: 30 wt % aqueous dispersion (used as dispersion in the examples) 90% polyvinyl acetate (MW 450 000 D), 9% Povidone K30, 1% sodium laurylsulfate, based on solids All percentages are wt %.

Examples 1-4: Aerosol Spray

General Procedure

Menthol was dissolved beforehand in abs. ethanol. Kollicoat SR 30 D was then added with stirring to the abs. ethanol/menthol mixture. This preparation was used to fill an aerosol can, the aerosol was can sealed with the aid of a crimping press and dimethyl ether was added under pressure through the valve. The fill level was 100 g.

| Ingredients | Example 1 | Example 2 |
|---|---|---|
| Kollicoat SR 30D | 13.33% | 13.33% |
| Abs. ethanol | 36.67% | 36.67% |
| Dimethyl ether | 49.00% | 48.00% |
| Menthol | 1.00% | 2.00% |
| Total | 100.00% | 100.00% |

Examples 3-4: Pump Sprays with Ethyl Acetate

General Procedure

Menthol was dissolved beforehand in abs. ethanol. Kollicoat SR 30 D was then added with stirring to the abs. ethanol/menthol mixture. Ethyl acetate was then added and the resulting solution was stirred for a few minutes. This preparation was dispensed into plastic pump spray bottles. The fill level was 100 g.

| Ingredients | Example 3 | Example 4 |
|---|---|---|
| Kollicoat SR 30D | 13.33% | 13.33% |
| Abs. ethanol | 36.67% | 36.67% |
| Ethyl acetate | 49.00% | 48.00% |
| Menthol | 1.00% | 2.00% |
| Total | 100.00% | 100.00% |

All pump and aerosol sprays prepared (Examples 1-4) were sprayed onto filter paper and PE film. After a brief drying time, sensory testing was carried out, and also after 2 h and 24 h and the results were documented.

Aerosol Spray

General Procedure

The aroma was firstly dissolved in an ethanol/water mixture (9:1 v/v). Kollidon SR was then added with constant stirring to the ethanol/water mixture. This preparation was used to fill an aerosol can, the aerosol can was crimped and dimethyl ether was added under pressure through the valve. The fill level was 50 g.

The sensory properties were tested as described above by spraying the sprays onto a carrier and after the periods of time specified in the tables.

Geraniol-containing sprays and sensory properties thereof

Example 5-7 Aerosol Spray with Geraniol

| Ingredients | Example 5 | Example 6 | Example 7 |
|---|---|---|---|
| Kollidon SR | 2.00% | 3.00% | 5.00% |
| Ethanol/water (9:1) | 58.00% | 57.00% | 55.00% |
| Dimethyl ether | 35.00% | 35.00% | 35.00% |
| Geraniol | 5.00% | 5.00% | 5.00% |
| Total | 100.00% | 100.00% | 100.00% |

Aerosol Spray with Geraniol

| Formulation | Start | 7 h | 1 day | 5 days | 6-7 days | 8-11 days | 12-14 days |
|---|---|---|---|---|---|---|---|
| Geraniol Extra (5% in EtOH) | ✓ | ✓ | X | X | X | X | X |
| 2% Koll.SR/5% geraniol | ✓ | ✓ | ✓ | ✓ | ✓ | ✓ | ✓ |
| 3% Koll.SR/5% geraniol | ✓ | ✓ | ✓ | ✓ | ✓ | ✓ | ✓ |
| 5% Koll.SR/5% geraniol | ✓ | ✓ | ✓ | ✓ | ✓ | ✓ | ✓ |

✓ odor perceptible
X odor no longer perceptible

Menthol-containing sprays and sensory properties thereof
Aerosolspray mit Menthol in Ethanol

Examples 8-11: Aerosol Spray with Menthol

| Ingredients | Example 8 | Example 9 | Example 10 | Example 11 |
|---|---|---|---|---|
| Kollidon SR | 1.00% | 2.00% | 3.00% | 5.00% |
| Ethanol/water (9:1) | 59.00% | 58.00% | 57.00% | 55.00% |
| Dimethyl ether | 39.00% | 39.00% | 39.00% | 39.00% |
| Menthol | 1.00% | 1.00% | 1.00% | 1.00% |
| Total | 100.00% | 100.00% | 100.00% | 100.00% |

Aerosol Spray with Menthol

| Formulation | Start | 1 h | 4 h | 7 h | 1 day | 5 days | 6-7 days | 9-12 days | 13-14 days |
|---|---|---|---|---|---|---|---|---|---|
| Menthol (5% in EtOH) | ✓ | ✓ | X | X | X | Stopped after 24 h, residue-free drying | | | |
| 1% Koll.SR/1% menthol | ✓ | ✓ | ✓ | ✓ | ✓ | ✓ | ✓ | X | X |
| 2% Koll.SR/1% menthol | ✓ | ✓ | ✓ | ✓ | ✓ | ✓ | ✓ | ✓ | X |
| 3% Koll.SR/1% menthol | ✓ | ✓ | ✓ | ✓ | ✓ | ✓ | ✓ | ✓ | ✓ |
| 5% Koll.SR/1% menthol | ✓ | ✓ | ✓ | ✓ | ✓ | ✓ | ✓ | ✓ | ✓ |

✓ odor perceptible
X odor no longer perceptible

Menthol perfume-containing sprays and sensory properties thereof
Aerosolspray mit Menthol

Examples 12-13: Aerosol Spray with Menthol Perfume

| Ingredients | Example 12 | Example 13 |
|---|---|---|
| Kollidon SR | 2.00% | 3.00% |
| Ethanol/water (9:1) | 58.00% | 57.00% |
| Dimethyl ether | 35.00% | 35.00% |
| Menthol perfume | 5.00% | 5.00% |
| Total | 100.00% | 100.00% |

Aerosol Spray with Menthol Perfume

| Formulation | Start | 7 h | 1 day | 5 days | 6-7 days | 8-11 days | 12-14 days |
|---|---|---|---|---|---|---|---|
| 2% Koll.SR/5% menthol perfume | ✓ | ✓ | ✓ | ✓ | ✓ | ✓ | ✓ |
| 3% Koll.SR/5% menthol perfume | ✓ | ✓ | ✓ | ✓ | ✓ | ✓ | ✓ |

✓ odor perceptible
X odor no longer perceptible

Pump Sprays without Ethyl Acetate

General Procedure

The aroma was firstly dissolved in an ethanol/water mixture (9:1 v/v). Kollidon SR was then added with constant stirring to the ethanol/water mixture.

Geraniol-containing sprays and sensory properties thereof

Examples 14-16: Pump Spray with Geraniol

| Ingredients | Example 14 | Example 15 | Example 16 |
|---|---|---|---|
| Kollidon SR | 2.00% | 3.00% | 5.00% |
| Ethanol/water (9:1) | 93.00% | 92.00% | 90.00% |
| Geraniol | 5.00% | 5.00% | 5.00% |
| Total | 100.00% | 100.00% | 100.00% |

Pump Spray with Geraniol

| Formulation | Start | 7 h | 1 day | 5 days | 6-7 days | 8-11 days | 12-14 days |
|---|---|---|---|---|---|---|---|
| Geraniol (5% in EtOH) | ✓ | ✓ | X | X | X | X | X |
| 2% Koll.SR/5% geraniol | ✓ | ✓ | ✓ | ✓ | ✓ | ✓ | X |
| 3% Koll.SR/5% geraniol | ✓ | ✓ | ✓ | ✓ | ✓ | ✓ | ✓ |
| 5% Koll.SR/5% geraniol | ✓ | ✓ | ✓ | ✓ | ✓ | ✓ | ✓ |

✓ odor perceptible
X odor no longer perceptible

Menthol perfume-containing sprays and sensory properties thereof

Example 17-18 Pump Spray with Menthol Perfume

| Ingredients | Example 17 | Example 18 |
|---|---|---|
| Kollidon SR | 2.00% | 3.00% |
| Ethanol/water (9:1) | 93.00% | 92.00% |
| Menthol perfume | 5.00% | 5.00% |
| Total | 100.00% | 100.00% |

Pump Spray with Menthol Perfume

| Formulation | Start | 7 h | 1 day | 5 days | 6-7 days | 8-11 days | 12-14 days |
|---|---|---|---|---|---|---|---|
| 2% Koll.SR/5% menthol perfume | ✓ | ✓ | ✓ | ✓ | ✓ | ✓ | ✓ |
| 3% Koll.SR/5% menthol perfume | ✓ | ✓ | ✓ | ✓ | ✓ | ✓ | ✓ |

✓ odor perceptible
X odor no longer perceptible

All pump and aerosol sprays prepared (Example 5-18) were sprayed onto glass plates. After a brief drying time, sensory testing was carried out, and also after 7 h, 1 day, 5 days, 6-7 days, 8-11 days and 12-14 days. The films were stored for two days at 33° C. in a drying cabinet and subsequently at an ambient temperature of 23° C.

The invention claimed is:

1. An odorant and flavoring formulation for topical application comprising, as a matrix former, a mixture of a water-insoluble polyvinyl acetate, having an average molecular weight Mw of 200,000 to 700,000 daltons and a water-soluble homopolymer of N-vinylpyrrolidone having a K value of 30;
   wherein a weight ratio of the polyvinyl acetate to the homopolymer of N-vinylpyrrolidone is about 4:1 to about 10:1.

2. The formulation according to claim 1, said formulation comprising the polyvinyl acetate having an average molecular weight $M_w$ of 400 000 to 500 000 daltons as the water-insoluble polymer and the homopolymer of N-vinylpyrrolidone having a K value of 30 as water-soluble polymer.

3. The formulation according to claim 1, said formulation additionally comprising 0.1 to 2 wt % sodium dodecylsulfate, based on the solids content of the formulation.

4. The formulation according to claim 1, said formulation additionally comprising 0.05 to 2 wt % silicon dioxide, based on the solids content of the formulation.

5. The formulation according to claim 1, said formulation comprising (i) 0.5 to 10 wt % matrix formers, (ii) 60 to 99.4 wt % solvent and (iii) 0.1 to 20 wt % of one or more perfumes, wherein the amounts are based on the total weight of the formulation.

6. The formulation according to claim 1, said formulation comprising a synthetic odorant from the group consisting of geraniol, linalool, linalyl acetate, pyranol, geranyl acetate, anisaldehyde, citral, citronellal, lysmeral, citronellol, rose oxide, tetrahydrolinalool, hydroxycitronellal, beta-ionone, and menthol.

7. The formulation according to claim 1 for use as a spray for topical applications.

8. The formulation according to claim 1 for use as a dermal spray for pharmaceutical or cosmetic applications to humans and animals.

9. The formulation according to claim 1 for use as a textile treatment.

10. The formulation according to claim 1, said formulation additionally comprising 0.1 to 2 wt % sodium dodecylsulfate, based on the solids content of the formulation; 0.05 to 2 wt % silicon dioxide, based on the solids content of the formulation; and (i) 0.5 to 10 wt % matrix formers, (ii) 60 to 99.4 wt % solvent and (iii) 0.1 to 20 wt % of one or more perfumes, wherein the amounts are based on the total weight of the formulation.

\* \* \* \* \*